United States Patent [19]
Lederer

[11] Patent Number: 6,060,986
[45] Date of Patent: May 9, 2000

[54] PROTECTIVE GLOVE BREACH MONITORING

[76] Inventor: Gabor Lederer, 28 Summit Ave., Hackensack, N.J. 07601

[21] Appl. No.: 09/099,425

[22] Filed: Jun. 18, 1998

[51] Int. Cl.⁷ .................................................. G08B 21/00
[52] U.S. Cl. ........................ 340/540; 340/604; 340/647; 128/917
[58] Field of Search .................. 340/605, 647, 340/540, 603, 604; 128/897, 917; 324/556, 557, 559; 606/34

[56] References Cited

U.S. PATENT DOCUMENTS

| | | | |
|---|---|---|---|
| 5,157,379 | 10/1992 | Dennison | 340/540 |
| 5,204,632 | 4/1993 | Leach | 324/557 |
| 5,351,008 | 9/1994 | Leach et al. | 324/557 |
| 5,430,434 | 7/1995 | Lederer et al. | 340/540 |
| 5,448,177 | 9/1995 | Thompson | 324/557 |
| 5,600,250 | 2/1997 | Thompson | 324/557 |
| 5,734,323 | 3/1998 | Hermes et al. | 340/540 |

*Primary Examiner*—Daniel J. Wu
*Assistant Examiner*—Van T. Trieu

*Attorney, Agent, or Firm*—Israel Nissenbaum

[57] ABSTRACT

A manipulating protective glove structure for use with non-conductive, hazardous materials, or materials sensitive to contamination, in a sealed environment, e.g., glove box. The glove structure embodies components which provide monitoring and signaling to the user, of a breach, in the glove structure. The outer surface of the manipulating glove itself is made electrically conductive by conductivity treatment of by inserting the glove into a thin conductive glove member which is sized to tightly cover the outer surface of the manipulating glove. An isolated electrical wire is electrically mounted to a the conductive outer surface with prevention of ingreee of air (with possible contamination). An electrical monitoring device is electrically connected to the user's skin and to the outer conductive layer via the electrical wire. The user's perspiration or a moisturizer cream used on the user's skin completes an electrical circuit between the user and the outer conductive layer with a breach in the manipulating glove. In an alternative embodiment, a second consuctive glove is positioned on the interior surface of the manipulating glove and electrical connection is between the inner and outer layers without electrical connection to either the user or object (or patient in a surgical procedure).

7 Claims, 1 Drawing Sheet

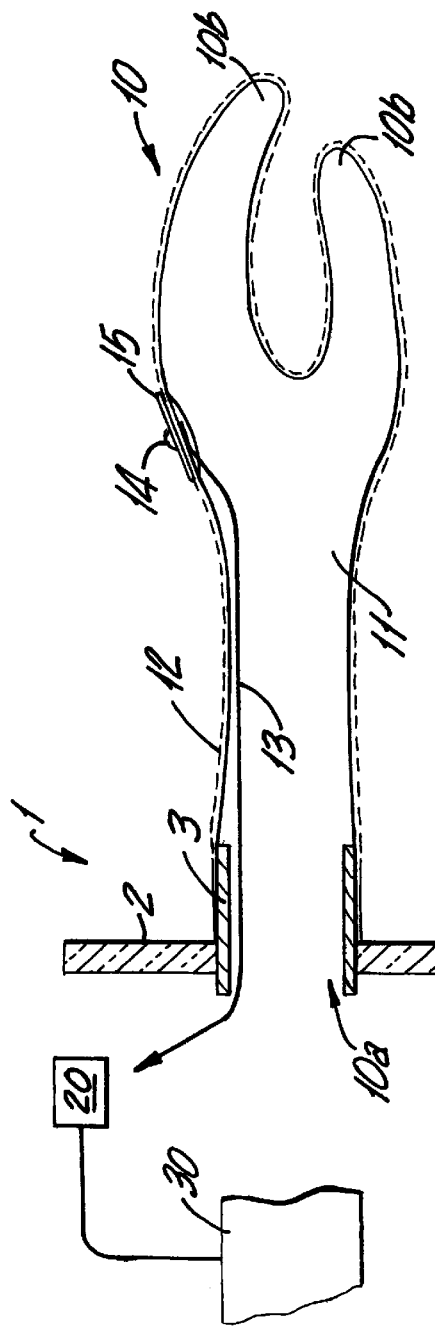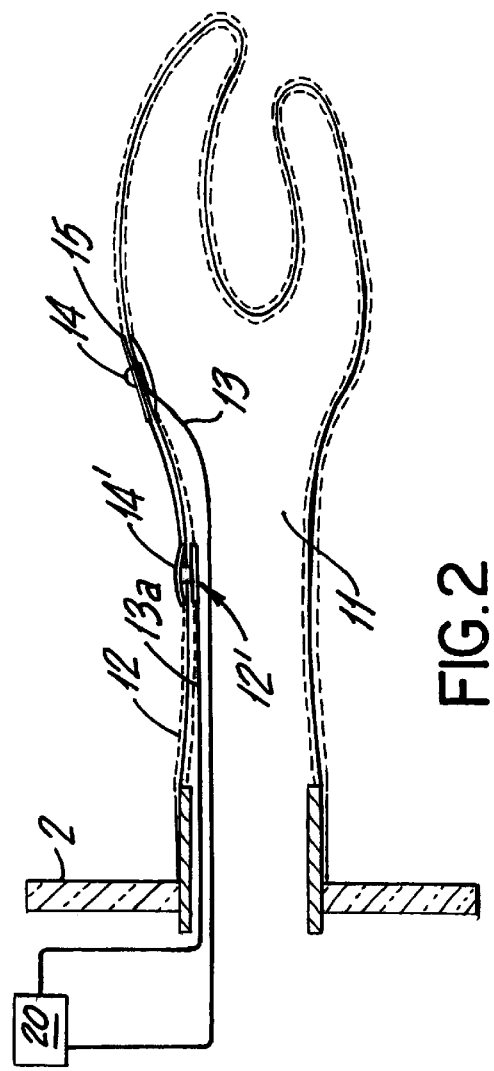

PROTECTIVE GLOVE BREACH MONITORING

FIELD OF THE INVENTION

This invention relates to the monitoring of breaches, i.e., inadvertently developed holes in manipulating protective gloves such as used in surgical or chemical procedures and with glove boxes where hazardous or contamination-sensitive materials are being handled.

BACKGROUND OF THE INVENTION

Devices for the continuous monitoring of breaches in protective gloves used with handling of chemicals, pharmaceuticals and particularly in surgical procedures, have been available for some time. These devices operate on the basic principle of a breach serving to permit the automatic effecting of a completed electrical circuit between the user and the person (in surgical procedures) or object (such as chemicals) being manipulated by the user. In all such devices the person or object (as applicable) is connected to the monitoring circuitry. When used in conjunction with the monitoring devices, the gloves are used in an electrically conductive environment, such as with electrolyte containing body fluids of the patient in surgical procedures, where a breach in the glove results in a direct conductive bridge between the person being operated upon, and the user, such as a surgeon (or other surgical personnel) wearing the glove. Similar electrical connection is effected between and object and a chemist or lab technician but only if the object is in an electrically conductive environment. A monitoring device such as described in applicant's prior U.S. Pat. No. 5,430,434, issued Jul. 4, 1995, the disclosure of which is incorporated herein by reference thereto, detects the completion of the electrical circuit and effects the appropriate alarm (audible, visual or vibration) to the user or wearer of the glove.

While surgical procedures often involve conductive fluids such as blood, chemical procedures involving powders or solids (i.e., with little or no electrical conductivity) and the like, provide difficulties with maintaining electrical connection for completion of a circuit. Accordingly, it is the practice in such situations to periodically check for breaches, e.g., pinholes by application of a vacuum to the glove or by dipping the glove into a conductive fluid bath which is kept as part of the circuit to the monitoring device. These checks however require that work being effected with the gloves be interrupted with loss of productive work time. Heretofore, it has not been possible to provide a constant monitoring of glove condition while the glove is being used in a non-electrically conducting environment. Thus, in said patent and in the other prior art patents it is required that a conductive material from the working (and connected by wire) environment (e.g., blood or other body fluids or chemicals in conductive solution or suspension emanating from the person or object) provide the electrical bridging for completion of the electrical circuit necessary for sounding the alarm. These devices, as currently configured, are however incapable of detecting breaches in a glove in an environment of non-conductive materials such as powder, or if the object or person being operated on is not electrically connected by wire to the device. Accordingly, breaches in gloves generally and particularly, as used in glove boxes such as with silicon chips, wafers, chemical and surgical processes, wherein even the tiniest contamination can detrimentally affect production, remain undetected, because of the lack of a conductive environment.

SUMMARY OF THE INVENTION

It is accordingly an object of the present invention to provide a modified glove structure capable of being reliably utilized with prior art electronic breach monitoring devices for the detection of breaches in gloves used in a non-conductive work environment.

It is a further object of the present invention to provide a glove structure which enables the providing of a requisite circuit through a breach in a glove for the closing of a circuit and the effective of an alarm, even without any wire connection to the object.

It is yet another object of the present invention to provide a glove structure which is independent of the user and the object with respect to the closure of a circuit and the effecting of an alarm indicative of a breach.

Generally the present invention comprises a structure for a protective (protective refers to both protection of the user and the object being manipulated or patient during surgery) manipulating surgical or material handling glove which glove is used to maintain electrical isolation and an hermetic seal between a user, i.e., manipulator, and a work environment of a hazardous nature or of a contamination sensitive nature such as in a glove box for handling of dangerous or bio-hazard chemicals, to prevent contamination of sensitive silicon chips, wafers, chemicals. The invention is also suitable in a surgical environment with materials which may be detrimental to either the user (e.g., HIV) or the patient (bacterial contamination) or to the bio-chemical or pharmaceutical environment. The modified glove structure permits either the user's own perspiration or pre-applied conductive hand coatings to effect the requisite circuit closure through a breach in the non-conductive glove member, for triggering an alarm, even in an otherwise non-conductive, non-object wired environment. In a further embodiment of the invention, the requisite circuit closure and alarm are effected irrespective of the user.

In accordance with the present invention an electrically non-conductive glove member is closely contained within or integrated with an outer electrically conductive layer or coating, with said conductive layer being electrically connected to an electrically activated breach detection and alarm device by electrical connection means which is preferably insulated. Said glove structure further comprises means for electrically isolating and hermetically sealing a user from the conductive layer except through a breach in the manipulating glove structure. The interior of the glove, i.e., a second inner conductive layer or the user himself/herself, is also electrically connected to the detection and alarm device whereby a breach in the non-conductive manipulating glove member results in completion of the circuit between the user and the outer conductive layer via perspiration or conductive material preplaced on the user's hand (a source of conductive fluid always present as an inherent part of glove usage), through the breach whereby the detection and alarm device is activated for the triggering of an alarm.

These and other objects, features and advantages of the present invention will become more evident from the following discussion and drawings in which:

BRIEF DESCRIPTION OF THE DRAWINGS

FIG. 1 is a side sectioned view of a first embodiment of a glove structure of the present invention as affixed within a glove box environment; and FIG. 2 is a side sectioned view of a second embodiment of a glove structure as affixed with a glove box environment.

DETAILED DESCRIPTION OF THE INVENTION

In accordance with the present invention, protective gloves, including the neoprene type gloves such as are commonly utilized in glove box environments or latex gloves commonly used as protective devices are provided at least exteriorally and preferably interiorally as well with secondary glove elements such as of latex. Alternatively, the protective glove is itself made surface conductive. These inner and outer glove elements (or the outer or the outer and inner surfaces of the protective glove itself) are initially made electrically conductive with the grafting or chemically etching of conductive materials such as conductive carbon or metal whiskers therein and over the entire surfaces thereof to enable detection of a breach of the manipulating glove at any point in contact therewith.

Alternatively, the interior and exterior glove elements are precoated by known means of plastic metallization, with metallic layers, and the conductive wires are electrically connected directly to the conductive layers. The actual manipulating gloves may have shallow surfaces thereof made conductive without the need for additional glove elements.

In a preferred embodiment of the present invention the conductivity of the outer surface of the neoprene gloves used in glove boxes (and which faces the interior of the glove box) is altered to about 10–100 kOhm/sq. inch resistance, to a depth of about 0.1 to 0.3 mils as an alteration of the molecular structure of the surface and not a peelable glued surface which may contaminate elements within the glove box.

In accordance with the present invention it is not necessary to effect an electrical connection with a patient or objects being worked on and in one embodiment herein electrical connection is not even required to the user of the glove.

DETAILED DESCRIPTION OF THE DRAWINGS AND THE PREFERRED EMBODIMENTS

With reference to the drawings, in FIG. 1, a manipulating glove 10 is shown as being affixed, via hermetic seal 3 in a wall 2 of glove box 1. The user's hand is inserted through glove aperture 10a and into fitment with manipulating fingers 10b. Glove 10 is comprised of manipulating glove member 11 and outer coating or outer thin conductive glove member 12. Conductive wire 13 is electrically attached to the outer coating or glove member 12 via metal rivet 14 and metal washer 15. In order to maintain hermeticity, the conductive wire 13 is drawn along the interior of the glove member 11 (rather than through the wall 2 though the present invention also encompasses a conductive element extending outside the glove), to an exteriorally disposed monitoring and alarm device 20 (shown schematically as a box). As shown, with the conductive wire 13 being drawn through the glove, it is insulated from electrical contact with the skin of the user's hand in order to prevent a direct short circuit connection therebetween. In addition, the area of the washer and rivet and the affixation of conductive wire thereto is hermetically sealed with sealant and insulator (they may be one element) to effect both electrical and hermetic isolation between the interior and exterior of the glove 10.

A second connection is made between the user's hand 30 and the alarm device 20, whereby loss of electrical isolation (i.e., a breach of the glove 10) results in completion of a circuit in the monitoring device and the effecting of an alarm as a warning of the breach. Even the slight perspiration, or an initially applied conductive moisturizer cream, on the user's hand, results in completion of an electrical circuit between the interior and exterior of the glove member as an indication of a breach. The exterior working environment may accordingly be entirely non-conductive, e.g., with powder pharmaceuticals or other chemicals, without affecting the ability to detect a breach.

In a second embodiment shown in FIG. 2, a second conductive layer or coating 12', is attached to the interior surface of the manipulating glove 11 whereby such glove 11 is closely sandwiched by the conductive layers or coatings 12 and 12'. In such embodiment the user is independent from the monitoring and alarm device. Instead, electrical connection is to the outer layer with wire connector 13 and rivet and washer 14 and 15 respectively as shown in FIG. 1. A second wire connection 13a is effected between inner conductive layer 12' and the alarm device 20 via rivet connector 14' which is insulated from electrical connection with the outer layer 12 (the connection between rivet connector 14' and the glove is hermetically sealed to maintain the absolute separation of the interior and exterior of the glove. With a breach in the glove member 11 and 12' perspiration from the user's hand can effect the requisite completion of the electrical circuit and triggering of the alarm.

In such latter embodiment, the user is not part of the circuit and may accordingly be physically isolated therefrom by use of a cotton glove if the user has latex allergies or the like making direct contact with the conductive layers untenable provided that a conductive material remains available within or without the glove in order to conductively bridge the breach.

It is understood that the above description and drawings are merely exemplary of the present invention and that changes in structure, components and composition of the elements are possible without departing from the scope of the present invention as defined in the following claims.

What is claimed is:

1. A structure for detecting breaches in an electrically non-conductive protective manipulating glove member, said structure comprising:
   a) said manipulating glove member;
   b) an outer electrically conductive layer as an outer surface of the glove member,
   c) said outer conductive layer being electrically connected to an electrically activated breach detection and alarm device by first electrically conductive connection means,
   d) means for electrically isolating a hand of a user from the outer conductive layer except through a breach in the manipulating glove structure;
   e) second electrically conductive connection means electrically connected to an electrically conductive member within the glove; and
   f) means for completing an electrical circuit between the outer conductive layer and the electrically conductive member within the glove only through said breach thereby resulting in completion of the circuit to the alarm device for triggering of an alarm indicating a breach in the glove member, wherein, with said breach, said outer conductive member and conductive member within the glove remain separated from each other and wherein said means for completing the electrical circuit therebetween comprises said electrically conductive member within the glove and the outer conductive layer being adapted to be electrically bridged only by a fluid conductive material introduced and contained within the glove, at a position adjacent to the electrically conductive inner surface of the glove.

2. The structure of claim 1, wherein the conductive member within the glove comprises the user's hand.

3. The structure of claim 1, wherein the conductive member within the glove comprises a second inner conductive layer as an interior surface of the non-conductive glove member.

4. The structure of claim 1, wherein the non-conductive glove member is hermetically affixed to a glove box for exterior manipulation of items contained within the glove box.

5. The structure of claim 1, wherein the means for completing an electrical circuit between the outer electrically conductive layer and the electrically conductive member within the glove comprises perspiration from the user's hand within the glove, wherein the outer electrically conductive layer and the conductive member within the glove are adapted such that the perspiration is normally positioned to be proximate and sufficient to effect said completion of the circuit through a breach in the glove member.

6. The structure of claim 1, wherein the means for completing an electrical circuit between the outer electrically conductive layer and the electrically conductive member within the glove comprises a conductive fluid material pre-applied to the user's hand within the glove.

7. The structure of claim 1 wherein the outer electrically conductive layer and the electrically conductive member within the glove, comprise opposite integral surface portions of the glove material, with said opposite integral surface portions each comprising integral electrical conductive means.

* * * * *